(12) United States Patent
Priebe et al.

(10) Patent No.: US 8,299,033 B2
(45) Date of Patent: Oct. 30, 2012

(54) IODO-HEXOSE COMPOUNDS USEFUL TO TREAT CANCER

(75) Inventors: Waldemar Priebe, Houston, TX (US); Slawomir Szymanski, Houston, TX (US); Izabela Fokt, Houston, TX (US); Charles Conrad, Houston, TX (US); Timothy Madden, Sugar Land, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 53 days.

(21) Appl. No.: 12/581,550

(22) Filed: Oct. 19, 2009

(65) Prior Publication Data

US 2010/0152121 A1 Jun. 17, 2010

Related U.S. Application Data

(63) Continuation of application No. PCT/US2008/060511, filed on Apr. 16, 2008.

(60) Provisional application No. 60/912,349, filed on Apr. 17, 2007.

(51) Int. Cl.
*A01N 43/04* (2006.01)
*A61K 31/70* (2006.01)
*C07H 1/00* (2006.01)

(52) U.S. Cl. ........................... 514/23; 536/1.11

(58) Field of Classification Search .................... 514/23; 536/1.11
See application file for complete search history.

(56) References Cited

U.S. PATENT DOCUMENTS

| 4,464,530 | A | 8/1984 | Matsumura et al. |
| 6,319,695 | B1 | 11/2001 | Wong et al. |
| 6,670,330 | B1 | 12/2003 | Lampidis et al. |
| 7,001,888 | B2 | 2/2006 | Tidmarsh et al. |

OTHER PUBLICATIONS

Gove et al., Webster's Third New International Dictionary, 1963, p. 1798.*
"Brain tumor", Merck Manual Online Edition, [retrieved on May 11, 2011]. Retrieved from the Internet http://www.merckmanuals.com/home/print/sec06/ch088/ch088b.html. Revision Feb. 2008.*
"What you need to know about cancer of the pancreas", published by National Institutes of Health, Sep. 2010, 48 pages.*
Costantino et al., A mild and easy one-pot procedure for the synthesis of 2-deoxysugars from glycals, Tetrahedron Letters, 2009, 41, 9177-9180.*
Greene et al, Protective Groups in Organic Synthesis, Third Edition, published by John Wiley & Sons, Inc, 1999, 48 pages.*
Fleming et al., Molecular Consequences of Silencing Mutant K-ras in Pancreatic Cancer Cells: Justification for K-ras—Directed Therapy, Mol. Cancer Research, 2005, 3(7), 413-423.*
Gould et al,Expression of Human Glucose Transporters in *Xenopus* Oocytes: Kinetic Characterization and Substrate Specificities of the Erythrocyte, Liver, and Brain Isoforms, Biochemistry, 1991, 30, 5139-5145.*
Pelicano et al., Oncogene. 2006, 25, 4633-4646.*
"Cancer treatment", Merck Manual Online Edition, [retrieved on Feb. 21, 2011]. Retrieved from the Internet http://www.merckmanuals.com/. Revision Aug. 2007.*
Danishefsky, S.J., et al., J. Am. Chem. Soc., (1987), vol. 109, 8119-8120.
Fowler, J.S., et al., J. of Labelled Compounds and Radiopharmaceuticals, (1979), vol. 16—No. 1, 7-9.
Gatley, S.J., J. of Nuclear Medicine, (2003), vol. 44—No. 7, 1082-1086.
Liu, K., et al., J. Org. Chem., (1992), vol. 57—No. 13, 3748-3750.
Morin, C., Tetrahedron Letters, (2006), vol. 47, 5055-5058.
Roush, W.R., et al., Organic Letters, (1999), vol. 1—No. 6, 899-902.

* cited by examiner

*Primary Examiner* — Eric S Olson
*Assistant Examiner* — Zhengfu Wang
(74) *Attorney, Agent, or Firm* — Nielsen IP Law LLC

(57) ABSTRACT

Methods of treating glioblastoma and pancreatic cancer are provided by the administration of a therapeutically effective amount of a iodo-hexose compound to a subject in need thereof. The subject disclosure includes methods of treating glioblastoma and pancreatic cancer comprising the administration of a therapeutically effective amount of a 2-deoxy-2-iodo-D-hexose compound including 2-deoxy-2-iodo-D-mannose, 2-deoxy-2-iodo-D-glucose, 2-deoxy-2-iodo-D-galactose, and/or 2-deoxy-2-iodo-D-talose to a subject in need thereof.

7 Claims, 9 Drawing Sheets

IODO-HEXOSE COMPOUNDS USEFUL TO TREAT CANCER

CROSS-REFERENCE TO RELATED APPLICATIONS

This application is a continuation of International Application No. PCT/US08/060,511 filed Apr. 16, 2008, which claims the benefit of U.S. Provisional Application Ser. No. 60/912,349 filed Apr. 17, 2007, both of which are incorporated herein by reference.

STATEMENT REGARDING FEDERALLY SPONSORED RESEARCH OR DEVELOPMENT

This disclosure was made with support under Grant Number CA101936, awarded by The National Institutes of Health. The U.S. government has certain rights in the invention.

BACKGROUND

Cancer treatment regimens are frequently challenged by multi-drug resistance as tumor cells adapt in response to drug treatment. Apoptosis, a type of programmed cell death, involves a series of biochemical events that lead to changes in cell morphology and death. The apoptotic process is executed in such a way as to safely dispose of cell fragments. By elucidating intracellular signal transduction pathways in cancer, however, it is possible for the structures and processes crucial for induction of cell death to be affected. Indeed, defective apoptosis processes have been implicated in numerous diseases. Excess apoptosis causes cell-loss diseases like ischemic damage. On the other hand, insufficient amounts of apoptosis results in uncontrolled cell proliferation such as cancer.

Changes occur with the progression of malignant gliomas, for example, that may be related to the activation of the PI-3K/AKT pathway (typically by PTEN loss or through growth factor activity such as EGFR). This survival pathway activates a number of adaptive changes that include among other things, a stimulus for angiogenesis, inhibitors to apoptosis, and metabolic shifts that promote activation of glycolysis, preferentially. Similarly, new targets of treatment for pancreatic cancer include targets of signal transduction pathways and molecules involved in angiogenesis, specifically, the ras oncogene signally pathway and inhibitors of the matrix metalloprotease (MMP) family.

Many cancers such as malignant gliomas and pancreatic cancer are intrinsically resistant to conventional therapies and represent significant therapeutic challenges. Malignant gliomas have an annual incidence of 6.4 cases per 100,000 (Central Brain Tumor Registry of the United States, 2002-2003) and are the most common subtype of primary brain tumors and the deadliest human cancers. In its most aggressive manifestation, glioblastoma multiforme (GBM), the median survival duration for patients ranges from 9 to 12 months, despite maximum treatment efforts. In fact, in approximately one-third of patients with GBM, tumors will continue to grow despite treatment with radiation and chemotherapy. Similarly, depending on the extent of the tumor at the time of diagnosis, the prognosis for pancreatic cancer is generally regarded as poor, with few victims still alive 5 years after diagnosis, and complete remission rare.

Further, in addition to the development of tumor resistance to treatments, another problem in treating malignant tumors is the toxicity of the treatment to normal tissues unaffected by disease. Often chemotherapy is targeted at killing rapidly-dividing cells regardless of whether those cells are normal or malignant. However, widespread cell death and the associated side effects of cancer treatments may not be necessary for tumor suppression if the growth control pathways of tumors can be disabled. For example, one approach is the use of therapy sensitization, i.e. using low dose of a standard treatment in combination with a drug that specifically targets crucial processes in the tumor cell, increasing the effects of the other drug.

Furthermore, combination therapies include vaccine based approaches in combination with the cytoreductive and immune-modulating elements of chemotherapy with the tumor cell cytotoxic specificity of immunotherapy. Combination therapies, however, are typically more difficult for both the patient and physician than therapies requiring only a single agent. Furthermore, certain tumors have an intrinsic resistance against radiotherapy and many chemotherapy modalities may be due to the differential and types of growth patterns that can represent various degrees of hypoxic regions within individual tumors. For example, gliomas can grow in predominately infiltrative fashion with little to no contrast enhancement seen on MRI scans versus more rapidly growing contrast enhancing mass lesions. Similarly, the early stages of pancreatic cancer can go undetected. Also, relative hypoxic areas can be seen both in the center of the rapidly growing tumor mass, which often has regions of necrosis associated with this, as well as some relatively hypoxic regions within the infiltrative component of the tumor as well. Accordingly, some of these relatively hypoxic regions may have cells, which are cycling at a slower rate and may therefore be resistant to chemotherapy agents.

Recently, certain proposed cancer therapies target the use of glycolytic inhibitors. This type of inhibitor is designed to benefit from the selectivity resulting when a cell switches from aerobic to anaerobic metabolism. Because of the growth of the tumor, cancer cells become removed from the blood (oxygen supply). Under hypoxia, the tumor cells up-regulate expression of both glucose transporters and glycolytic enzymes, in turn, favoring an increased uptake of the glucose analogs as compared to normal cells in an aerobic environment. Blocking glycolysis in a cell in the blood will not kill the cell because the cell survives by using oxygen to burn fat and protein in their mitochondria to produce energy (via energy-storing molecules such as ATP). By contrast, when glycolysis is blocked in cells in a hypoxic environment, the cell dies, because without oxygen, the cell is unable to produce energy via mitochondria) oxidation of fat and protein. Hence, while glycolytic inhibitors have shown promise to treat certain cancers, not all cancer cells exist in a hypoxic environment. Indeed, classic observations by Otto Warburg have demonstrated a preference of many tumors to preferentially utilize glycolysis for cellular energy production, even in the presence of adequate amounts of oxygen (termed oxidative glycolysis or the "Warburg effect"). This tumor adaptive response appears to hold true for malignant gliomas as well.

A need exists, therefore, for the treatment of cancers that show a resistance to chemotherapy, exhibit differential growth patterns or growth patterns that have various degrees of hypoxic regions within the tumor and/or have survival pathways which are a stimulus for angiogenesis or inhibit apoptosis.

SUMMARY

The present disclosure is directed to new iodo-hexose compounds and compositions and their application as pharmaceuticals for the treatment of disease. Methods of preventing, modulating and/or inhibiting tumor activity in a human or animal subject are also provided for the treatment diseases such as glioblastoma and pancreatic cancer.

The iodo-hexose compounds of the subject disclosure may be used in the treatment or prophylaxis of a disease or condition in which cancer plays an active role. Thus, in a broad aspect, the present disclosure also provides pharmaceutical compositions comprising one or more compounds of the present disclosure together with a pharmaceutically acceptable carrier, as well as methods of making and using the compounds and compositions. The present disclosure also provides methods for treating a cancer-mediated disorder in a patient in need of such treatment comprising administering to said patient a therapeutically effective amount of a compound or composition according to the present disclosure. The present disclosure also contemplates the use of compounds disclosed herein for use in the manufacture of a medicament for the treatment of a disease or condition ameliorated by the inhibition or modulation of cancerous tumors.

DRAWINGS

For a more complete understanding of the present disclosure, and the advantages thereof, reference is made to the following descriptions taken in conjunction with the accompanying drawings, in which.

DETAILED DESCRIPTION

Figure 1:
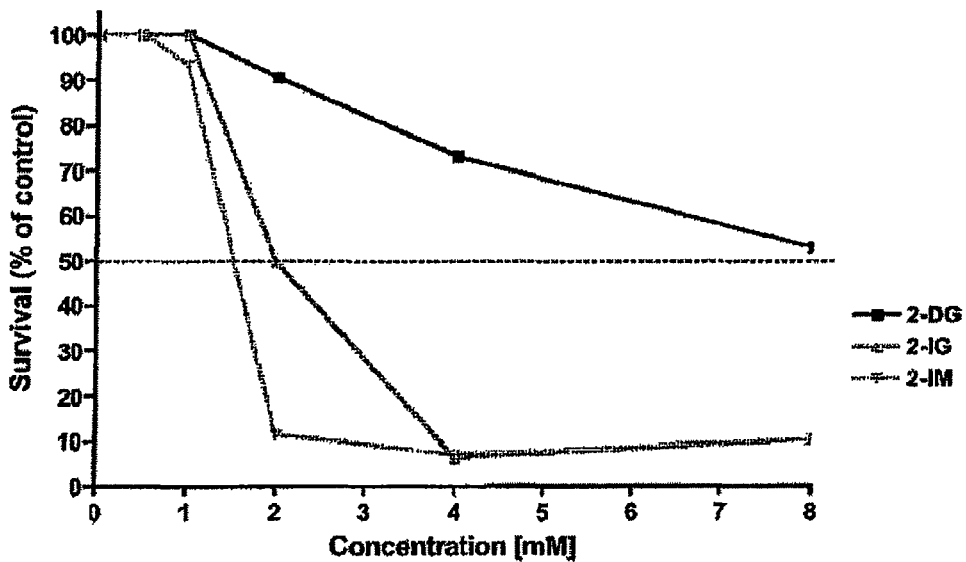
FIG. 1 shows activity comparison of 2-IM and 2-IG with 2-DG in glioma U251 brain tumor.

The present disclosure provides two novel iodo-hexose compounds, 2-deoxy-2-iodo-D-mannose (also referred to herein as "2-IM"), and 2-deoxy-2-iodo-D-talose (also referred to herein as "2-Ital") useful in the treatment of cancer. The disclosure further provides novel methods of treating glioblastoma and pancreatic cancer by administering to a subject in need thereof a therapeutic amount of 2-IM or 2-Ital. Moreover, novel methods of using two additional iodo-hexose compounds, 2-deoxy-2-iodo-D-glucose (also referred to herein as "2-IG" and "2-deoxy-2-glucopyranose" and "2-deoxy-2-iodo-D-glucose"), and 2-deoxy-2-iodo-D-galactose ("2-IGal") are described herein. The present disclosure also provides novel methods of making iodo-hexose compounds.

The chemical structures of the iodo-hexose compounds of the subject disclosure are as follows:

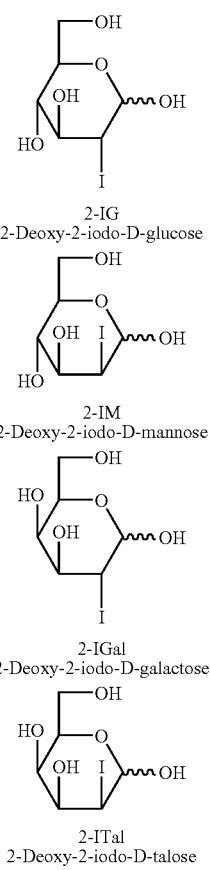

2-IG
2-Deoxy-2-iodo-D-glucose

2-IM
2-Deoxy-2-iodo-D-mannose

2-IGal
2-Deoxy-2-iodo-D-galactose

2-ITal
2-Deoxy-2-iodo-D-talose

The term "iodo-hexose compounds" includes compounds as described above which are also referred to herein sometimes as a "2-iodo-D-hexose compound" or a "2-deoxy-2-D-hexose compound."

Furthermore, as used herein, the terms below have the meanings indicated.

The term "combination therapy" means the administration of two or more therapeutic agents to treat a therapeutic condition or disorder described in the present disclosure. Such administration encompasses co-administration of these therapeutic agents in a substantially simultaneous manner, such as in a single capsule having a fixed ratio of active ingredients or in multiple, separate capsules for each active ingredient. In addition, such administration also encompasses use of each type of therapeutic agent in a sequential manner. In either case, the treatment regimen will provide beneficial effects of the drug combination in treating the conditions or disorders described herein.

The terms "coadministering" or "coadministration" are intended to encompass simultaneous or sequential administration of therapies. For example, co-administration may include administering both a glycolytic inhibitor and a chemotherapeutic agent in a single composition. It may also include simultaneous administration of a plurality of such compositions. Alternatively, co-administration may include administration of a plurality of such compositions at different times during the same period.

The phrase "therapeutically effective" is intended to qualify the amount of active ingredients used in the treatment of a disease or disorder. This amount will achieve the goal of reducing or eliminating the said disease or disorder.

The term "therapeutically acceptable" refers to those compounds (or salts, prodrugs, tautomers, zwitterionic forms, etc.) which are suitable for use in contact with the tissues of patients without undue toxicity, irritation, and allergic response, are commensurate with a reasonable benefit/risk ratio, and are effective for their intended use.

The terms "treating," "treatment" or "alleviation" refers to both therapeutic treatment and prophylactic or preventative measures, wherein the object is to prevent or slow the growth of a tumor, to reduce the size of tumor or to eliminate it entirely. The term "treatment" of a patient is intended to include prophylaxis.

The term "patient" means all mammals including humans. Examples of patients include humans, cows, dogs, cats, goats, sheep, pigs, and rabbits. Preferably, the patient is a human.

The term "prodrug" refers to a compound that is made more active in vivo. Certain compounds of the present disclosure may also exist as prodrugs, as described in *Hydrolysis in Drug and Prodrug Metabolism: Chemistry, Biochemistry, and Enzymology* (Testa, Bernard and Mayer, Joachim M. Wiley-VHCA, Zurich, Switzerland 2003). Prodrugs of the compounds described herein are structurally modified forms of the compound that readily undergo chemical changes under physiological conditions to provide the compound. Additionally, prodrugs can be converted to the compound by chemical or biochemical methods in an ex vivo environment. For example, prodrugs can be slowly converted to a compound when placed in a transdermal patch reservoir with a suitable enzyme or chemical reagent. Prodrugs are often useful because, in some situations, they may be easier to administer than the compound, or parent drug. They may, for instance, be bioavailable by oral administration whereas the parent drug is not. The prodrug may also have improved solubility in pharmaceutical compositions over the parent drug. A wide variety of prodrug derivatives are known in the art, such as those that rely on hydrolytic cleavage or oxidative activation of the prodrug. An example, without limitation, of a prodrug would be a compound which is administered as an ester (the "prodrug"), but then is metabolically hydrolyzed to the carboxylic acid, the active entity. Additional examples include peptidyl derivatives of a compound.

Accordingly, the subject disclosure provides a pharmaceutical formulation comprising a compound together with one or more pharmaceutically acceptable carriers thereof and optionally one or more other therapeutic ingredients. The carrier(s) must be "acceptable" in the sense of being compatible with the other ingredients of the formulation and not deleterious to the recipient thereof. Proper formulation is dependent upon the route of administration chosen. Any of the well-known techniques, carriers, and excipients may be used as suitable and as understood in the art; e.g., in Remington's Pharmaceutical Sciences. The pharmaceutical compositions of the present disclosure may be manufactured in a manner that is itself known, e.g., by means of conventional mixing, dissolving, granulating, levigating, emulsifying, encapsulating, entrapping or compression processes.

Certain suitable formulations for administration of the compounds of the subject disclosure include those suitable for oral, parenteral (including subcutaneous, intradermal, intramuscular, intravenous, intraarticular, and intramedullary), intraperitoneal, transmucosal, transdermal, rectal and topical (including dermal, buccal, sublingual and intraocular) administration although the most suitable route may depend upon, for example, the condition and disorder of the recipient. The formulations may conveniently be presented in unit dosage form and may be prepared by any of the methods well known in the art of pharmacy. All methods include the step of bringing into association a compound of the subject disclosure or a pharmaceutically acceptable salt, ester, prodrug or solvate thereof ("active ingredient") with the carrier which constitutes one or more accessory ingredients. In general, the formulations are prepared by uniformly and intimately bringing into association the active ingredient with liquid carriers or finely divided solid carriers or both and then, if necessary, shaping the product into the desired formulation.

Formulations of the present disclosure suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

Pharmaceutical preparations which can be used orally include tablets, push-fit capsules made of gelatin, as well as soft, sealed capsules made of gelatin and a plasticizer, such as glycerol or sorbitol. Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered compound moistened with an inert liquid diluent. The tablets may optionally be coated or scored and may be formulated so as to provide slow or controlled release of the active ingredient therein. All formulations for oral administration should be in dosages suitable for such administration. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. The formulations may be presented in unit-dose or multi-dose containers, for example sealed ampoules and vials, and may be stored in powder form or in a freeze-dried (lyophilized) condition requiring only the addition of the sterile liquid carrier, for example, saline or sterile pyrogen-free water, immediately prior to use. Extemporaneous injection solutions and suspensions may be prepared from sterile powders, granules and tablets of the kind previously described.

Formulations for parenteral administration include aqueous and non-aqueous (oily) sterile injection solutions of the active compounds which may contain antioxidants, buffers, bacteriostats and solutes which render the formulation isotonic with the blood of the intended recipient; and aqueous and non-aqueous sterile suspensions which may include suspending agents and thickening agents. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

For buccal or sublingual administration, the compositions may take the form of tablets, lozenges, pastilles, or gels formulated in conventional manner. Such compositions may comprise the active ingredient in a flavored basis such as sucrose and acacia or tragacanth.

The compounds may also be formulated in rectal compositions such as suppositories or retention enemas, e.g., containing conventional suppository bases such as cocoa butter, polyethylene glycol, or other glycerides. Preferred unit dosage formulations are those containing an effective dose, as herein below recited, or an appropriate fraction thereof, of the active ingredient.

It should be understood that in addition to the ingredients particularly mentioned above, the formulations of this disclosure may include other agents conventional in the art having regard to the type of formulation in question, for example those suitable for oral administration may include flavoring agents.

The compounds of the disclosure may be administered orally or via injection at a dose of from 0.1 to 500 mg/kg per day. The dose range for adult humans is generally from 5 mg to 2 g/day. Tablets or other forms of presentation provided in discrete units may conveniently contain an amount of compound of the disclosure which is effective at such dosage or as a multiple of the same, for instance, units containing 5 mg to 500 mg, usually around 10 mg to 200 mg.

The amount of active ingredient that may be combined with the carrier materials to produce a single dosage form will vary depending upon the host treated and the particular mode of administration.

The compounds of the subject disclosure can be administered in various modes, e.g. orally, topically, or by injection. The precise amount of compound administered to a patient will be the responsibility of the attendant physician. The specific dose level for any particular patient will depend upon a variety of factors including the activity of the specific compound employed, the age, body weight, general health, sex, diets, time of administration, route of administration, rate of excretion, drug combination, the precise disorder being treated, and the severity of the indication or condition being treated. Also, the route of administration may vary depending on the condition and its severity.

In certain instances, it may be appropriate to administer at least one of the compounds described herein (or a pharmaceutically acceptable salt, ester, or prodrug thereof) in combination with another therapeutic agent. By way of example only, if one of the side effects experienced by a patient upon receiving one of the compounds herein is hypertension, then it may be appropriate to administer an anti-hypertensive agent in combination with the initial therapeutic agent. Or, by way of example only, the therapeutic effectiveness of one of the compounds described herein may be enhanced by administration of an adjuvant (i.e., by itself the adjuvant may only have minimal therapeutic benefit, but in combination with another therapeutic agent, the overall therapeutic benefit to the patient is enhanced). Or, by way of example only, the benefit of experienced by a patient may be increased by administering one of the compounds described herein with another therapeutic agent (which also includes a therapeutic regimen) that also has therapeutic benefit. By way of example only, in a treatment for diabetes involving administration of one of the compounds described herein, increased therapeutic benefit may result by also providing the patient with another therapeutic agent for diabetes. In any case, regardless of the disease, disorder or condition being treated, the overall benefit experienced by the patient may simply be additive of the two therapeutic agents or the patient may experience a synergistic benefit.

Hence, the treatments defined herein may be applied as a sole therapy or may involve, in addition to at least one compound of the disclosure, one or more other substances and/or treatments. Such treatment may be achieved by way of the simultaneous, sequential or separate administration of the individual components of the treatment.

The compounds of this disclosure may also be useful in combination with known anti-cancer and cytotoxic agents and treatments such as radiation therapy. If formulated as a fixed dose, such combination products employ the compounds of this disclosure within the dosage range described herein and the other pharmaceutically active agent within its approved dosage range. 2-deoxy-2-iodo-D-hexose compounds may be used sequentially as part of a chemotherapeutic regimen also involving other anticancer or cytotoxic agents and/or in conjunction with non-chemotherapeutic treatments such as surgery or radiation therapy.

Specific, non-limiting examples of possible combination therapies include use of the compounds of the disclosure with chemotherapeutic agents. Chemotherapeutic agents include, but are not limited to, three main categories of therapeutic agents: (i) antiangiogenic agents such as, linomide, inhibitors of integrin alpha-beta 3 function, angiostatin, razoxane); (ii) cytostatic agents such as antiestrogens (for example, tamoxifen, toremifene, raloxifene, droloxifene, iodoxifene), progestogens (for example megestrol acetate), aromatase inhibitors (for example anastrozole, letrozole, borazole, exemestane), antihormones, antiprogestogens, antiandrogens (for example flutamide, nilutamide, bicalutamide, cyproterone acetate), LHRH agonists and antagonists (for example, gosereline acetate, leuprolide), inhibitors of testosterone 5-alpha-dihydroreductase (for example, finasteride), farnesyltransferase inhibitors, anti-invasion agents (for example, metalloproteinase inhibitors like marimastat and inhibitors of urokinase plasminogen activator receptor function) and inhibitors of growth factor function, (such growth factors include for example, EGF, FGF, platelet derived growth factor and hepatocyte growth factor such inhibitors include growth factor antibodies, growth factor receptor antibodies such as Avastin. (bevacizumab) and Erbitux. (cetuximab); tyrosine kinase inhibitors and serine/threonine kinase inhibitors); and (iii) antiproliferative/antineoplastic drugs and combinations thereof, as used in medical oncology, such as antimetabolites (for example antifolates like methotrexate, fluoropyrimidines like 5-fluorouracil, purine and adenosine analogues, cytosine arabinoside); Intercalating antitumor antibiotics (for example anthracyclines like doxorubicin, daunomycin, epirubicin and idarubicin, mitomycin-C, dactinomycin, mithramycin); platinum derivatives (for example cisplatin, carboplatin); alkylating agents (for example nitrogen mustard, melphalan, chlorambucil, busulphan, cyclophosphamide, ifosfamide nitrosoureas, thiotepa; antimitotic agents (for example vinca alkaloids like vincristine and taxoids like Taxol (paclitaxel), Taxotere (docetaxel) and newer microbtubule agents such as epothilone analogs, discodermolide analogs, and eleutherobin analogs); topoisomerase inhibitors (for example epipodophyllotoxins like etoposide and teniposide, amsacrine, topotecan); cell cycle inhibitors; biological response modifiers and proteasome inhibitors such as Velcade (bortezomib).

In any case, the multiple therapeutic agents (at least one of which is a compound of the present disclosure) may be administered in any order or even simultaneously. If simultaneously, the multiple therapeutic agents may be provided in a single, unified form, or in multiple forms (by way of example only, either as a single pill or as two separate pills). One of the therapeutic agents may be given in multiple doses, or both may be given as multiple doses. If not simultaneous, the timing between the multiple doses may be any duration of time ranging from a few minutes to four weeks.

Thus, in another aspect, the present disclosure provides methods for treating cancer-mediated disorders in a human or animal subject in need of such treatment comprising administering to said subject an amount of a compound of the present disclosure effective to reduce or prevent said disorder in the subject in combination with at least one additional agent for the treatment of said disorder that is known in the art. In a related aspect, the present disclosure provides therapeutic compositions comprising at least one compound of the present disclosure in combination with one or more additional agents for the treatment of cancer-mediated disorders. As described below, the compounds of the subject disclosure have been shown to be particularly useful in treating glioblastoma and tumors of the central nervous system, and pancreatic cancer.

"Tumors of the central nervous system" can mean and include any abnormal growth of tissue within the brain, spinal cord or other central-nervous-system tissue, either benign or malignant. It particularly includes gliomas such as pilocytic astrocytoma, low-grade astrocytoma, anaplastic astrocytoma and glioblastoma multiforme (GBM or glioblastoma). "Tumors of the central nervous system" also includes other types of benign or malignant gliomas such as brain stem glioma, ependymoma, ganglioneuroma, juvenile pilocytic glioma, mixed glioma, oligodendroglioma and optic nerve glioma. "Tumors of the central nervous system" also includes non-gliomas such as chordoma, craniopharyngioma, medulloblastoma, meningioma, pineal tumors, pituitary adenoma, primitive neuroectodermal tumors, schwannoma, vascular tumors and neurofibromas. Finally, "Tumors of the central nervous system also includes metastatic tumors where malignant cells have spread to the central nervous system from other parts of the body.

Besides being useful for human treatment, the compounds and formulations of the present disclosure are also useful for veterinary treatment of companion animals, exotic animals and farm animals, including mammals, rodents, and the like. More preferred animals include horses, dogs, and cats.

All references, patents or applications, U.S. or foreign, cited in the application are hereby incorporated by reference as if written herein.

Below is provided the novel synthesis and reaction schemes for making the iodo-hexose compounds of the subject disclosure including novel compounds, deoxy-2-iodo-D-mannose, and 2-deoxy-2-iodo-D-talose, and the other iodo-hexose compounds, 2-deoxy-2-iodo-D-galactose, and 2-dexoy-2-iodo-D-glucose.

Synthetic Methods for Preparing Compounds

In one embodiment, the iodo-hexose compounds of the subject disclosure can be synthesized by contacting peracetyl-D-glucal with N-iodosuccinimide in the presence of water, separating diastereomeric 2-deoxy-2-iodo-D-hexose compounds; and removing the acetate protecting groups.

In some embodiments, the following scheme(s) can be used to practice the present disclosure.

Scheme 1 The iodo-hexose compounds of the subject disclosure can be synthesized using the following general synthetic procedure as set forth in Scheme 1:

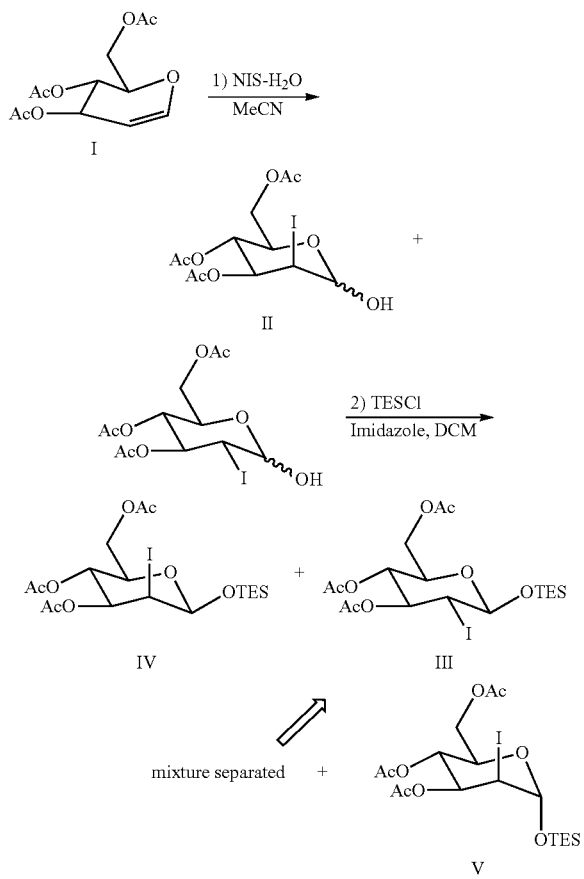

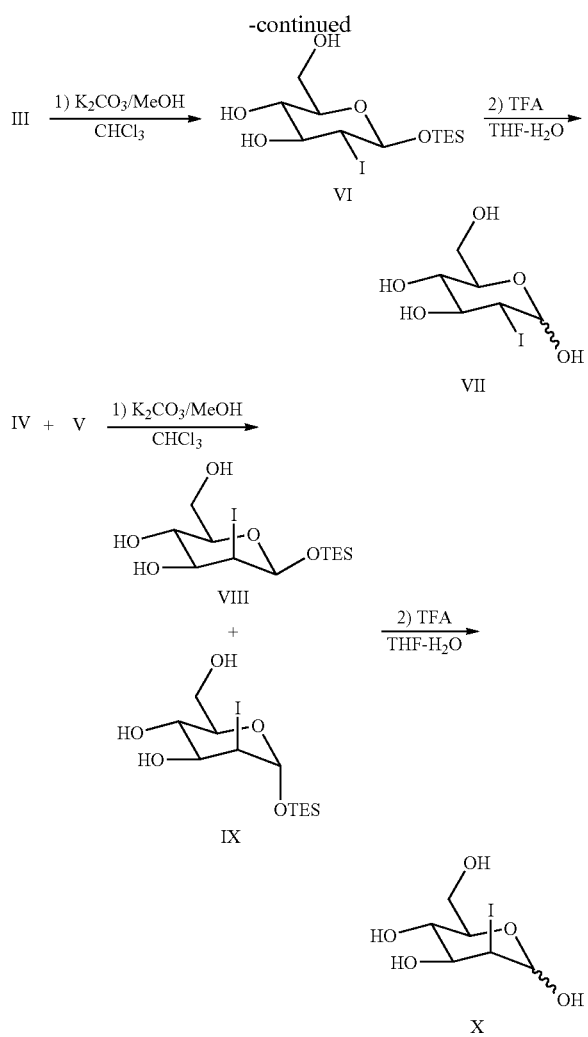

3,4,6-Tri-O-acetyl-glucal (I) (10 g, 36.7 mmol) was dissolved in mixture of tetrahydrofuran:acetonitrile (2:1, v/v) (100 mL). N-Iodosuccinimide (12 g, 53.3 mmol) followed by water (0.5 mL, 27.7 mmol) were added, and the reaction mixture was stirred at room temperature for 24 hours. The reaction mixture was diluted with dichloromethane (300 mL). Obtained solution was washed with sodium thiosulfate (10% water solution), (2×250 mL), then with water until neutral, brine and dried over sodium sulfate. Drying agent was filtered off, solvents were evaporated to dryness and products were separated by column chromatography (SilicaGel 60, Merck) using hexanes, hexanes:ethyl acetate 4:1 as eluents. Fractions contained mixture of 3,4,6-tri-O-acetyl-2-deoxy-2-iodo-D-glucose and 3,4,6-tri-O-acetyl-2-deoxy-2-iodo-D-mannose (II) were pooled together and evaporated to dryness. (II) (11.5 g, yield 70%) was obtained. Such mixture (11 g) was dissolved in dichloromethane (100 mL). Imidazole (15 g, 0.22 mol) followed by chlorotriethylsilane (8 g) were added. The reaction mixture was stirred at room temperature overnight. Dichloromethane (300 mL) was added and the mixture was washed with water until neutral, then dried over sodium sulfate. After solids and solvents were removed, products were separated by column chromatography (SilicaGel 60, Merck) using hexanes, hexanes:ethyl acetate 9:1, 4:1 as eluents, to give:

2-deoxy-2-iodo-3,4,6-tri-O-acetyl-1-O-triethylsilyl-β-D-glucopyranose (III) (0.71 g) (yield 5%), 2-deoxy-2-iodo-3,4, 6-tri-O-acetyl-1-O-triethylsilyl-β-D-mannopyranose (IV) (2.6 g) (yield 18.5%), and 2-deoxy-2-iodo-3,4,6-tri-O-acetyl-1-O-triethylsilyl-α-D-mannopyranose (V) (5.4 g) (40%).

2-Deoxy-2-iodo-3,4,6-tri-O-acetyl-1-O-triethylsilyl-β-D-glucopyranose (III)

¹HNMR (CDCl₃, δ) ppm: 5.31 (dd, 1H, J=11.1 Hz, J=9.0 Hz, H-3), 4.94 (dd, 1H, J=J=10.0 Hz, H-4), 4.92 (d, 1H, J=8.6 Hz, H-1), 4.21 (dd, 1H, J=12.1 Hz, J=5.8 Hz, H-6), 4.14 (dd, 1H, J=12.1 Hz, J=2.3 Hz, H-6), 3.98 (dd, 1H, J=11.2 Hz, J=8.6 Hz, H-2), 3.77 (dddd, 1H, J=10.0 Hz, J=5.8 Hz, J=2.3 Hz, H-5), 2.10, 2.09, 2.03 (3s, 3H ea, OAc), 1.02 (t, 9H, J=8.0 Hz, CH₃), 0.70 (q, 6H, J=8.0 Hz, CH₂).

2-Deoxy-2-iodo-3,4,6-tri-O-acetyl-1-O-triethylsilyl-O-D-mannopyranose (IV)

¹HNMR (CDCl₃, δ) ppm: 5.34 (dd, 1H, J=J=9.7 Hz, H-4), 4.64 (dd, 1H, J=4.1 Hz, J=1.0 Hz, H-2), 4.49 (dd, 1H, J=9.5 Hz, J=4.2 Hz, H-3), 4.20 (dd, 1H, J=12.1 Hz, J=2.7 Hz, H-6), 4.15 (dd, 1H, J=12.1 Hz, J=6.2 Hz, H-6), 4.03 (bs, 1H, H-1), 3.69 (dddd, 1H, J=9.2 Hz, J=6.2 Hz, J=2.7 Hz, H-5), 2.12, 2.09, 2.07 (3s, 3H ea, OAc), 0.98 (t, 9H, J=8.0 Hz, CH₃), 0.74-0.59 (m, 6H, CH₂).

2-Deoxy-2-iodo-3,4,6-tri-O-acetyl-1-O-triethylsilyl-α-D-mannopyranose (V)

¹HNMR (CDCl₃, δ) ppm: 5.50 (bs, 1H, H-1), 5.38 (dd, 1H, J=9.5 Hz, H-4), 4.75 (dd, 1H, J=9.5 Hz, J=4.0 Hz, H-3), 4.48 (d, 1H, J=4.0 Hz, H-2), 4.25-4.19 (m, 2H, H-5, H-6), 4.12 (d, 1H, J=10 Hz, H-6), 2.11, 2.09, 2.07 (3s, 3H ea, OAc), 0.99 (t, 9H, J=8.0 Hz, CH₃), 0.68 (q, 6H, J=8.0 Hz, CH₂).

Subsequently, the 2-deoxy-2-iodo-3,4,6-tri-O-acetyl-1-O-triethylsilyl-β-D-glucopyranose (III) (0.7 g) was dissolved in the mixture of chloroform:methanol (7:3 v/v) (15 mL). Potassium carbonate (4 g) was added, and reaction mixture was stirred at room temperature until substrate deacetylation has been completed. Inorganic salts were filtered off and solvents were evaporated. Such obtained product was purified by column chromatography (SilicaGel 60, Merck) using chloroform and chloroform:methanol 99:1 as eluents, to give (0.1 g) of 2-deoxy-2-iodo-1-O-triethylsilyl-β-D-glucopyranose (VI) (yield 20%).

2-Deoxy-2-iodo-1-O-triethylsilyl-β-D-glucopyranose (VI)

¹HNMR (CDCl₃, δ) ppm: 5.31 (dd, 1H, J=11.1 Hz, J=9.0 Hz, H-3), 4.94 (dd, 1H, J=J=10 Hz, H-4), 4.92 (d, 1H, J=8.6 Hz, H-1), 4.21 (dd, 1H, J=12.1 Hz, J=5.8 Hz, H-6), 4.14 (dd, 1H, J=12.1 Hz, J=2.3 Hz, H-6), 3.89 (dd, 1H, J=11.2 Hz, J=8.6 Hz, H-2), 3.77 (ddd, 1H, J=9.8 Hz, J=5.7 Hz, J=2.2 Hz, H-5), 2.10, 2.09, 2.03 (3s, 3H ea, OAc), 1.02 (t, 9H, J=7.9 Hz, CH₃), 0.70 (q, 6H, J=7.9 Hz, CH₂).

The same procedure was applied for 2-deoxy-2-iodo-3,4, 6-tri-O-acetyl-1-β-triethylsilylα-D-mannopyranose (V) (5.4 g) to obtain 2-deoxy-2-iodo-1-O-triethylsilyl-α-D-mannopyranose (IX) (3.5 g, yield 85%).

2-Deoxy-2-iodo-1-O-triethylsilyl-α-D-mannopyranose (IX)

¹HNMR (DMSO-d6, δ) ppm: 5.50 (bs, 2H, H-1 and OH), 5.04 (d, 1H, J=5.7 Hz, OH), 4.49 (dd, 1H, J=5.8 Hz, OH), 4.28 (dd, 1H, J=3.9 Hz, J=1.0 Hz, H-2), 3.63-3.60 (m, 2H, H-5, H-6), 3.49 (ddd, 1H, J=12.2 Hz, J=6.3 Hz, H-6), 3.39 (ddd, 1H, J=9.0 Hz, J=5.7 Hz, H-4), 3.05 (dd, 1H, J=8.3 Hz, J=J=4.0 Hz, H-3), 0.94 (t, 9H, J=8.0 Hz, CH₃), 0.62 (q, 6H, J=8.0 Hz, CH₂)

EXAMPLE 1

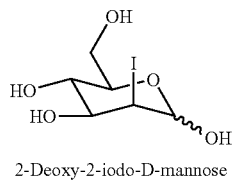

2-Deoxy-2-iodo-D-mannose $^1$HNMR (DMSO-d6, δ) ppm: 5.29 (bs, 1H, H-1α), 4.34 (bs, 1H, H-2β), 4.27 (bs, 1H, H-2α), 3.94 (bs, 1H, H-1β), 3.66-3.61 (m, 3H, H-5β, H-6α, H-6β), 3.48-3.36 (m, 2H, H-6α, H-6β), 3.29 (dd, 1H, J=J=9.1 Hz, H-4α), 3.23 (dd, 1H, J=J=9.0 Hz, H-4β), 3.17-3.14 (m, 1H, H-5α), 2.99 (dd, 1H, J=9.1 Hz, J=3.5 Hz, H-3α), 2.87 (dd, 1H, J=9.0 Hz, J=3.5 Hz, H-3β).

$^{13}$C NMR (DMSO-d6, δ) ppm: 95.4 (C-1β), 91.9 (C-1α), 78.3 (C-5α), 74.5 (C-5β), 71.4 (C-3β), 69.9 (C-4α), 69.6 (C-4β), 67.9 (C-3α), 61.8 (C-6α, C-6β), 49.6 (C-2β), 43.2 (C-2β). FAB-MS: m/z 288.97

Mixture of 2-deoxy-2-iodo-1-O-triethylsilyl-α-D-mannopyranose (IX) and 1-O-triethylsilyl-2-iodo-2-deoxy-β-D-mannopyranose (VIII) (total of 3.55 g) was dissolved in THF (50 mL), water (20 mL) and trifluoroacetic acid (0.7 mL) and stirred at room temperature. Progress of the reaction was monitored by TLC and after substrate disappearance reaction mixture was washed with dichloromethane (5×10 mL). The remaining water solution was lyophilized and such obtained crude solid residue was purified by column chromatography (SilicaGel 60, Merck) using chloroform and chloroform:methanol 9:1, 7:3 as eluents, to give 2.3 g of 2-deoxy-2-iodo-D-mannose (X). Yield 90%.

EXAMPLE 2

VII

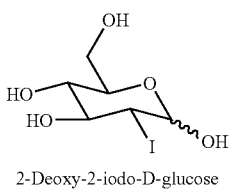

2-Deoxy-2-iodo-D-glucose $^1$HNMR (D$_2$O, δ) ppm: 5.32 (d, 1H, J=3 Hz, H-1α), 4.91 (d, 1H, J=8.8 Hz, H-1β), 3.91 (dd, 1H, J=11.1 Hz, J=3.0 Hz, H-2α), 3.85-3.76 (m, 3H, H-4α, H-4β, H-6α), 3.70-3.57 (m, 3H, H-2β, H-5α, H-6β), 3.46-3.36 (m, 1H, H-5β), 3.36 (dd, 1H, J=J=10 Hz, H-3α), 3.30 (dd, 1H, J=J=9.6 Hz, H-3β).

$^{13}$CNMR (D$_2$O, δ) ppm: 96.7 (C-1β), 93.4 (C-1α), 77.1 (C-5α), 76.0 (C-5β), 73.4 (C-4α), 72.1 (C-4β), 70.7 (C-3β) 70.3 (C-3α), 60.7 (C-6β), 60.5 (C-6α), 36.6 (C-2β), 33.1 (C-2α). FAB-MS: m/z 288.98

Mixture of 2-deoxy-2-iodo-1-O-triethylsilyl-β-D-glucopyranose (VI) (0.1 g), THF (2 mL), water (0.5 mL) and trifluoroacetic acid (0.1 mL) was prepared and stirred at room temperature. Progress of the reaction was monitored by TLC and after substrate disappearance reaction mixture was washed with dichloromethane (5×10 mL). The remaining water solution was lyophilized and such obtained crude solid residue was purified by column chromatography (SilicaGel 60, Merck) using chloroform, chloroform:methanol 9:1, 7:3 as eluents, to give (0.05 g) of 2-deoxy-2-iodo-D-glucose (VII). Yield 70%.

Treatment of Gliomas and Pancreatic Cancer

The present disclosure provides novel 2-deoxy-2-iodo-D-hexose compounds useful for the treatment of tumors of the central nervous system, such as gliomas as well as pancreatic cancer. The present disclosure provides methods to inhibit tumor cell proliferation whether the cells are in a hypoxic or normoxic environment, using 2-deoxy-2-iodo-D-hexose compounds of the subject disclosure alone, or in combination with other anti-tumor treatments, including but not limited to cytotoxic agents that target normoxic cells, anti-angiogenic agents, radiation therapy, and surgery.

Therapeutic options for malignant gliomas remain quite limited. This is due in part to the intrinsic resistance of the cells to many chemotherapy options that are available. It may also be due in part to the differential growth patterns which malignant gliomas exhibit. Namely, gliomas can grow in predominately in infiltrative fashion with little to no contrast enhancement seen on MRI scans versus more rapidly growing contrast enhancing mass lesions. Many studies have indicated that these different types of growth patterns also represent various degrees of hypoxic regions within individual tumors. Relative hypoxic areas can be seen both in the center of the rapidly growing tumor mass, which often has regions of necrosis associated with this, as well as some relatively hypoxic regions within the infiltrative component of the tumor as well. Accordingly, some of these relatively hypoxic regions may have cells, which are cycling at a slower rate and may therefore be more resistant to many chemotherapy agents. Additionally, the observations by Warburg who described a preference of many tumors to undergo glycolysis even in the presence of adequate amounts of oxygen (termed oxidative glycolysis or the "Warburg effect") appears to hold true for malignant gliomas as well.

As shown in the figures, the iodo-hexose compounds, particularly, 2-deoxy-2-iodo-D-hexose compounds such as 2-deoxy-2-iodo-D-mannose, 2-deoxy-2-iodo-D-glucose, 2-deoxy-2-iodo-D-galactose, and 2-deoxy-2-iodo-D-talose have been shown to be useful in the treatment of glioblastoma and pancreatic cancer.

The data provided herein verifies the effectiveness of the disclosure and confirms that 2-deoxy-2-iodo-D-hexose compounds are toxic to select tumor cell types growing under normoxia. Furthermore, the data provided herein demonstrates that 2-deoxy-2-iodo-D-mannose and 2-deoxy-2-iodo-D-glucose are effective at killing tumor cells in either hypoxic or normoxic conditions.

While the mechanism of action is currently not completely understood, it is believed that the chemical properties of iodine make it possible for the 2-deoxy-2-iodo-D-hexoses to undergo chemical reactions involving free radicals or nucleophilic substitution, and such reactions can lead to the formation of covalent bonds with interacting proteins, for example.

The increased cytoxicity of iodo-hexose compounds include a possible radical forming reaction manifold. Such radical reactions may lead to increased cellular toxicity, including necrosis. Denef, J. F.; Many, M. C.; van den Hove, M. F. "Iodine-induced thyroid inhibition and cell necrosis: two consequences of the same free-radical mediated mechanism" "Mol Cell Endocrinol. 1996 Jul. 23; 121(1):101-3. Additionally, iodides possess superb electrophilic character providing alkylating agents for bimolecular nucleophilic substitution reactions (S$_N$2) with important biomolecules, such as cysteine residues of proteins. Dennehy, M. K.; Richards, K. A.; Wernke, G. R.; Shyr, Y;. Liebler, D. C., "Cytosolic and nuclear protein targets of thiol-reactive electrophiles," Chem. Res. Toxicol. 2006 Jan;. 19(1):20-9. In support of an $S_N2$ mechanism applicants have observed rapid reaction of cysteine with 2-deoxy-2-iodo-D-hexoses.

As discussed below, FIGS. 1-17 demonstrate the in vitro activity of the 2-deoxy-2-iodo-D-hexose compounds described herein against a variety of tumor cell lines and under hypoxic and normoxic conditions. The observed increase in activity of 2-deoxy-2-iodo-D-hexose compounds may be attributed, in part, to the reactivity of iodine when compared to other halogen derivatives. Also, as shown, 2-deoxy-2-iodo-D-mannose and 2-deoxy-2-iodo-D-glucose were equally potent under normoxia and hypoxia in all tested tumor cell lines including U87, U251, U373, D54, Colo357-FG, Colo357-L3.6 and AsPc-1.

The activity of the iodo-hexose compounds of the subject disclosure is illustrated in the following assay. Other compounds listed above, which have not yet been made and/or tested, are predicted to have activity in these assay as well.

EXAMPLES

To create the data provided in FIGS. 1-17, a "Promega" cell titer 96 Aqueous Non-Radioactive cell proliferation assay kit (G5430) was used. On Day 1, a 96 well plate was used to plate $3 \times 10^3$ cells in 100 µL of 10% FBS in each well. The growth medium for the cells was DMEM-F12 medium. On Day 2, the cells were then treated with the appropriate monosaccharide over the appropriate dynamic concentration range and then incubated at 37° C. for 72 hours in a 5% $CO_2$ atmosphere. On Day 5, 2.0 mL of MTS solution and 100 µL of PMS were combined. A 20 µL aliquot of the combined MTS and PMS solution were introduced into each well and incubation continued at 37° C. for 1 to 4 hours in a humidified 5% $CO_2$ atmosphere. Finally, the absorbance at 490 nm was recorded and the data plotted as absorbance versus drug exposure.

A standard MTT colorimetric assay can be used as an alternative to generate cytoxicity data. For example, cells can be incubated with a particular concentration of 2-IM, 2-IG, 2-DG, 2-IGal, or 2-Ital (FIG. 1-17) for 72 hours. Cell growth and survival can be estimated by MTT assay. Mosmann, T., "Rapid Colorimetric Assay for Cellular Growth and Survival: Application to Proliferation and Cytotoxicity Assays." J. Immunol. Meth. 1983, 65, 55-63. Wilson, A. P., "*Cytotoxicity and Viability Assays* in Animal Cell Culture: A Practical Approach," 3rd ed. (ed. Masters, J. R. W.) Oxford University Press: Oxford 2000, Vol. 1, pp 175-219.

Figure 6:
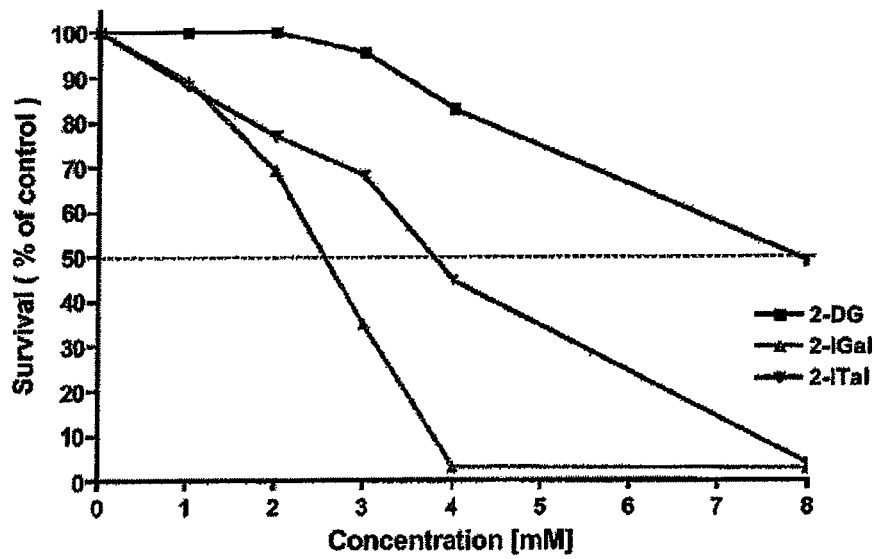
FIG. 6 shows activity comparison of 2-IGal and 2-ITal with 2-DG in glioma U251 brain tumor.
Figure 7:
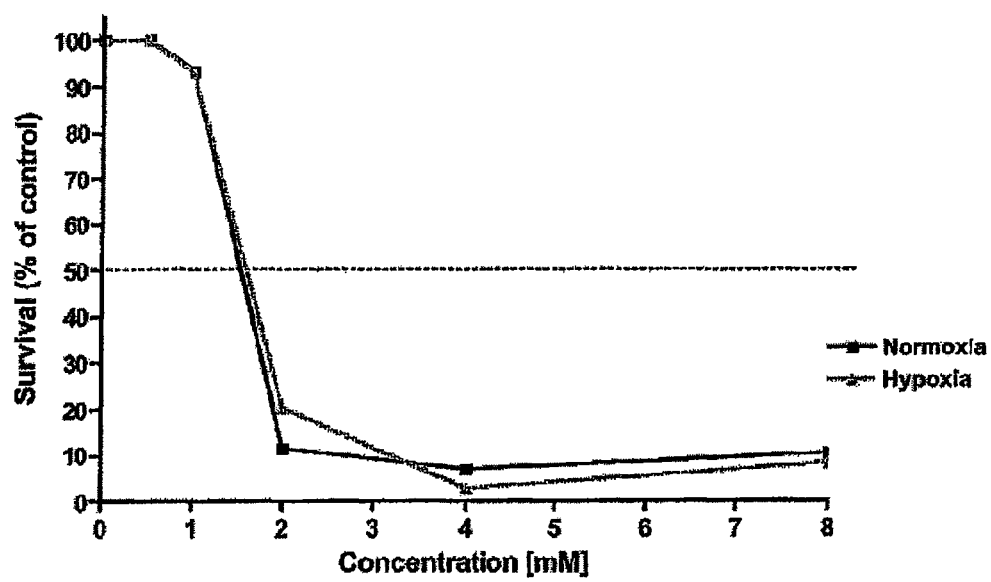
FIG. 7 shows activity comparison of 2-IM in glioma U251 brain tumor under normoxia and hypoxia.
Figure 12:
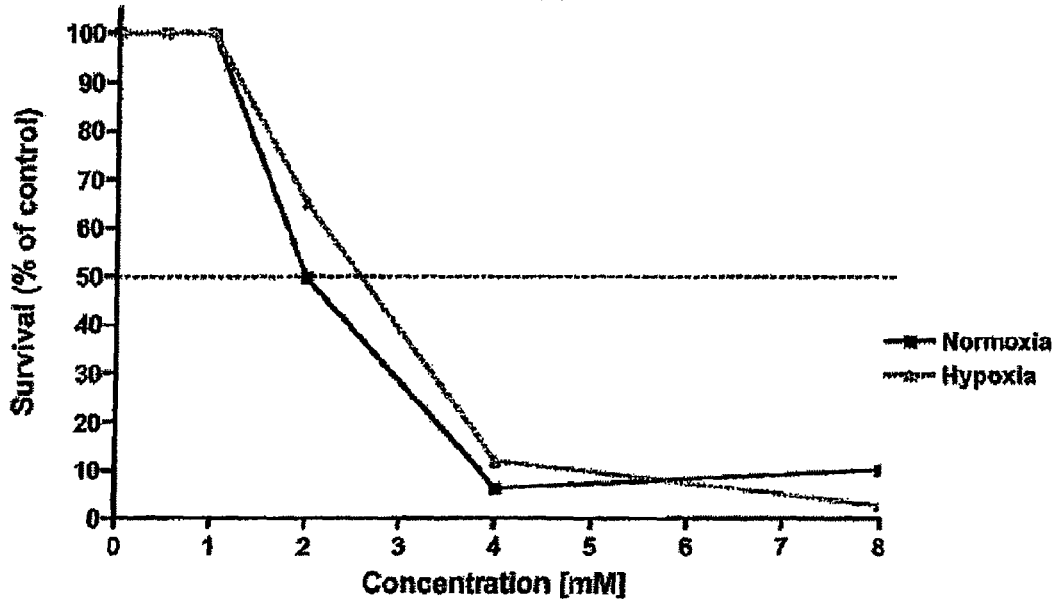
FIG. 12 shows activity comparison of 2-IG in U251 brain tumor under normoxia and hypoxia.

FIG. 1 shows activity comparison of 2-IM and 2-IG with 2-DG in glioma U251 brain tumor. Similarly, FIG. 6 shows activity comparison of 2-IGal and 2-ITal with 2-DG in glioma U251 brain tumor. FIG. 7 shows activity comparison of 2-IM in glioma U251 brain tumor under normoxia and hypoxia. FIG. 12 shows activity comparison of 2-IG in U251 brain tumor under normoxia and hypoxia.

Figure 2:
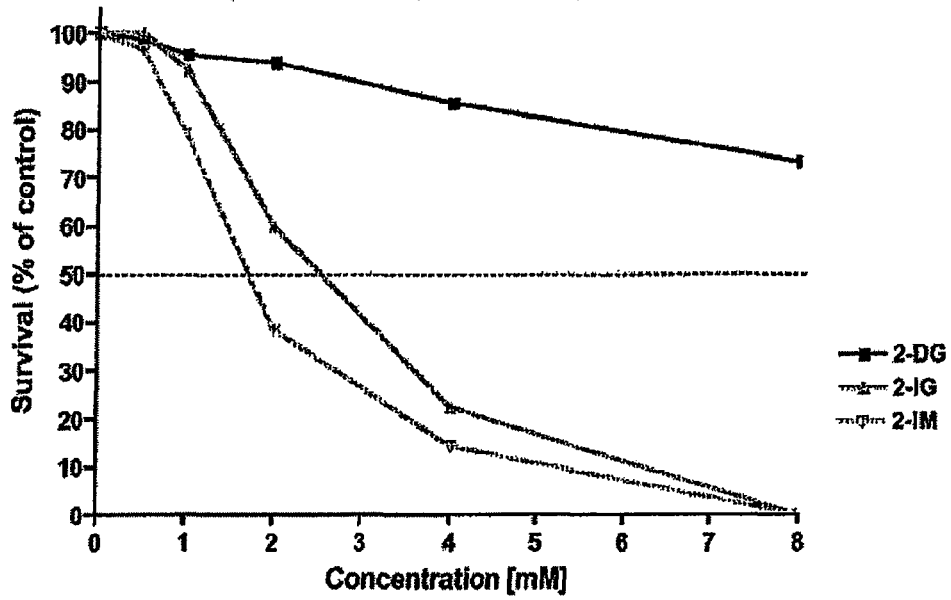
FIG. 2 shows activity comparison of 2-IM and 2-IG with 2-DG in glioma U373 brain tumor.
Figure 13:
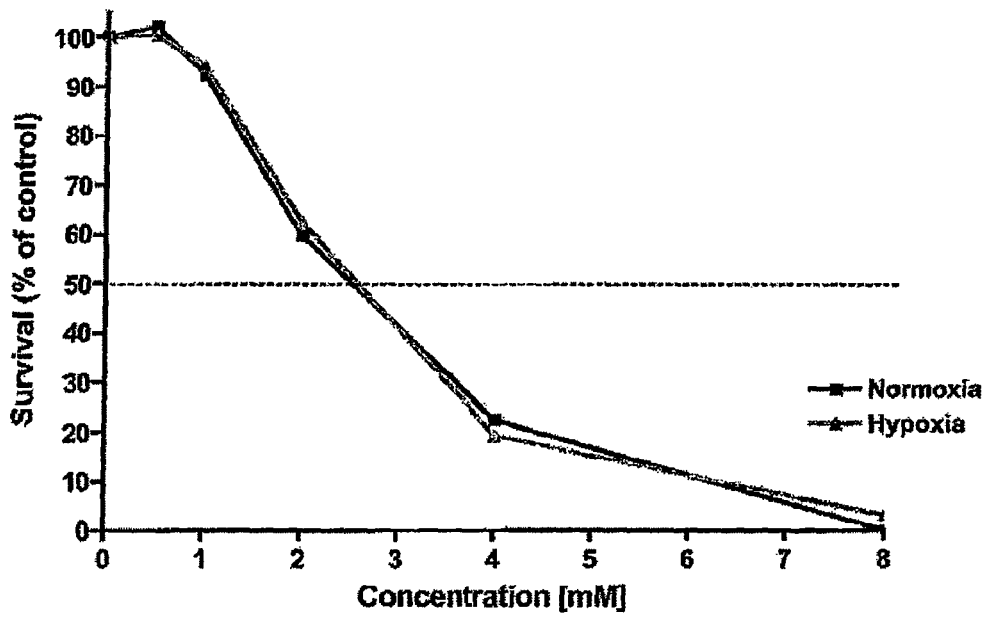
FIG. 13 shows activity comparison of 2-IG in U373 brain tumor under normoxia and hypoxia.

FIG. 2 shows activity comparison of 2-IM and 2-IG with 2-DG in glioma U373 brain tumor. FIG. 13 shows activity comparison of 2-IO in U373 brain tumor under normoxia and hypoxia.

Figure 3:
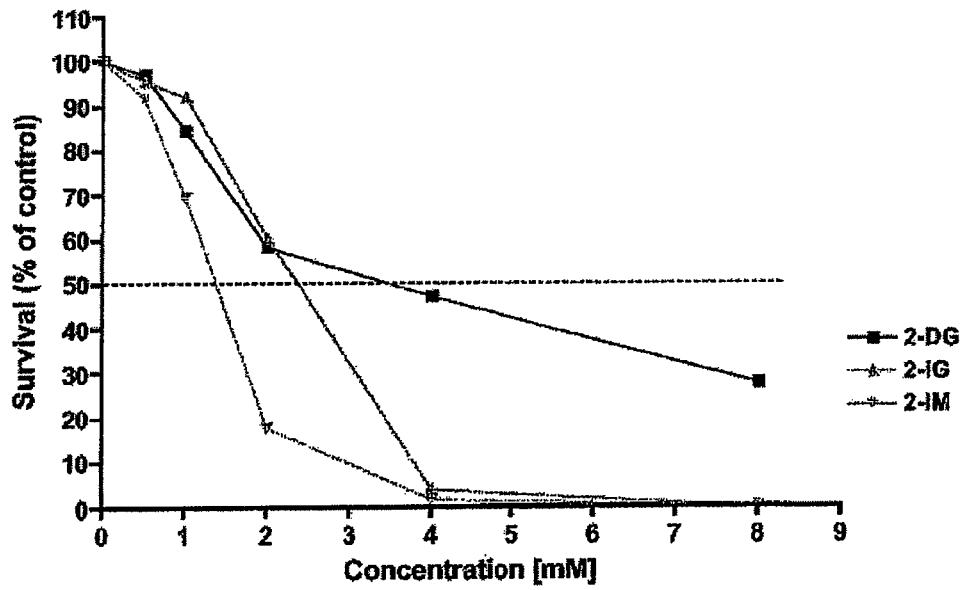
FIG. 3 shows activity comparison of 2-IM and 2-IG with 2-DG in glioma D54 brain tumor.

FIG. 3 shows activity comparison of 2-IM and 2-IG with 2-DG in glioma D54 brain tumor.

Figure 4:
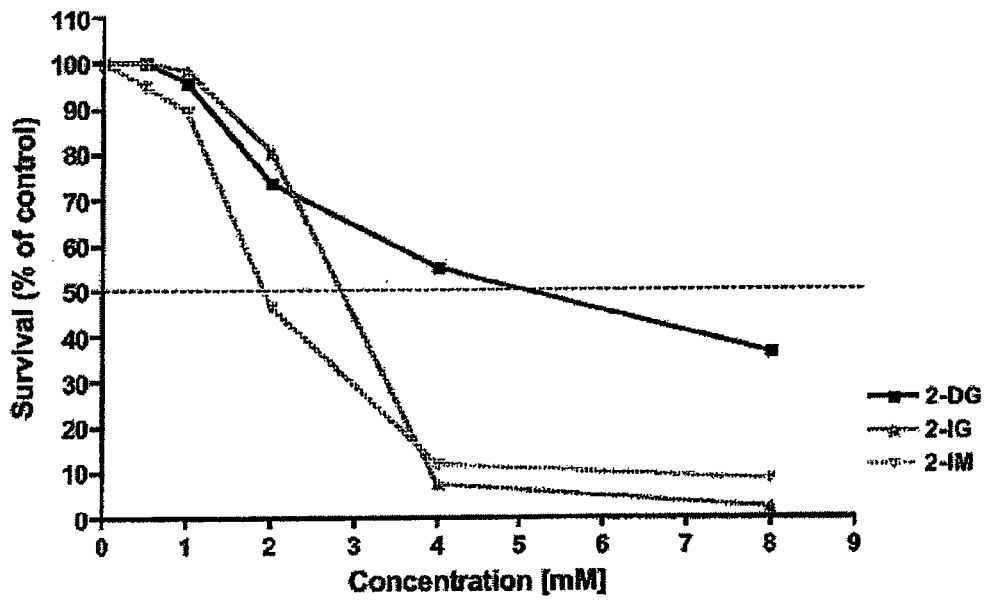
FIG. 4 shows activity comparison of 2-IM and 2-IG with 2-DG in glioma U87 brain tumor.
Figure 8:
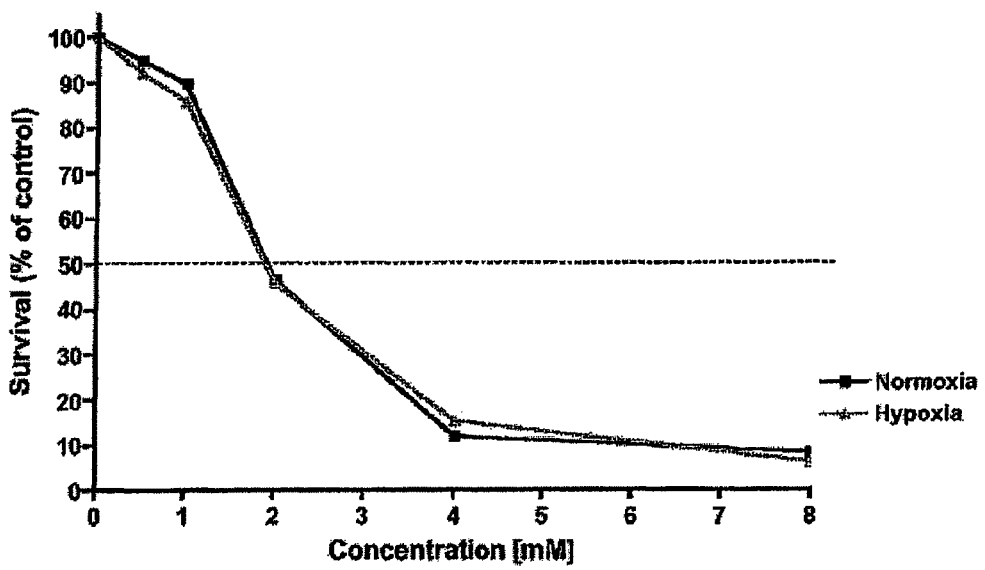
FIG. 8 shows activity comparison of 2-IM in glioma U87 brain tumor under normoxia and hypoxia.
Figure 14:
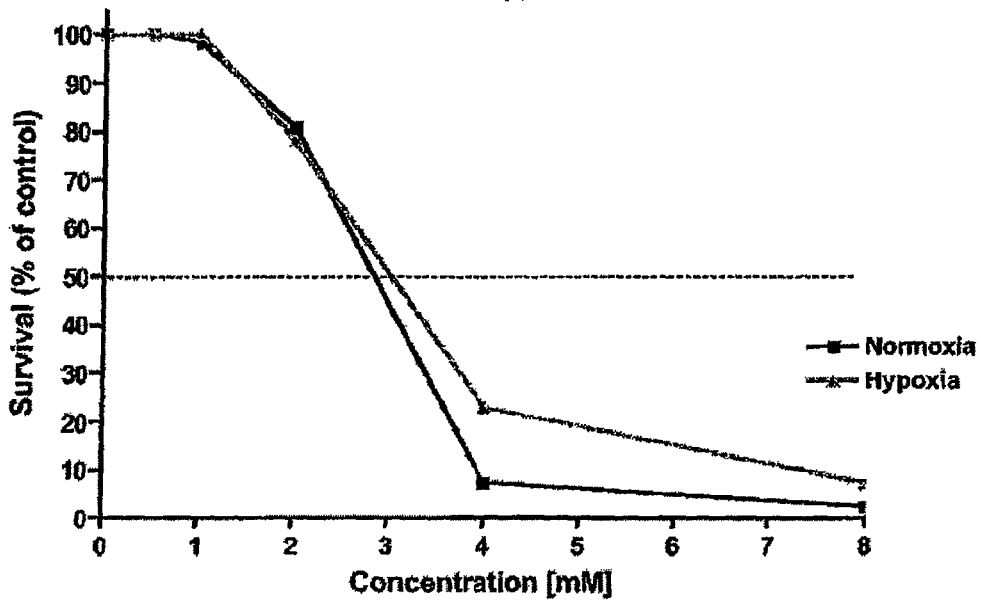
FIG. 14 shows activity comparison of 2-IG in U87 brain tumor under normoxia and hypoxia.

FIG. 4 shows activity comparison of 2-IM and 2-IG with 2-DG in glioma U87 brain tumor. FIG. 8 shows activity comparison of 2-IM in glioma U87 brain tumor under normoxia and hypoxia. FIG. 14 shows activity comparison of 2-IG in U87 brain tumor under normoxia and hypoxia.

Figure 5:
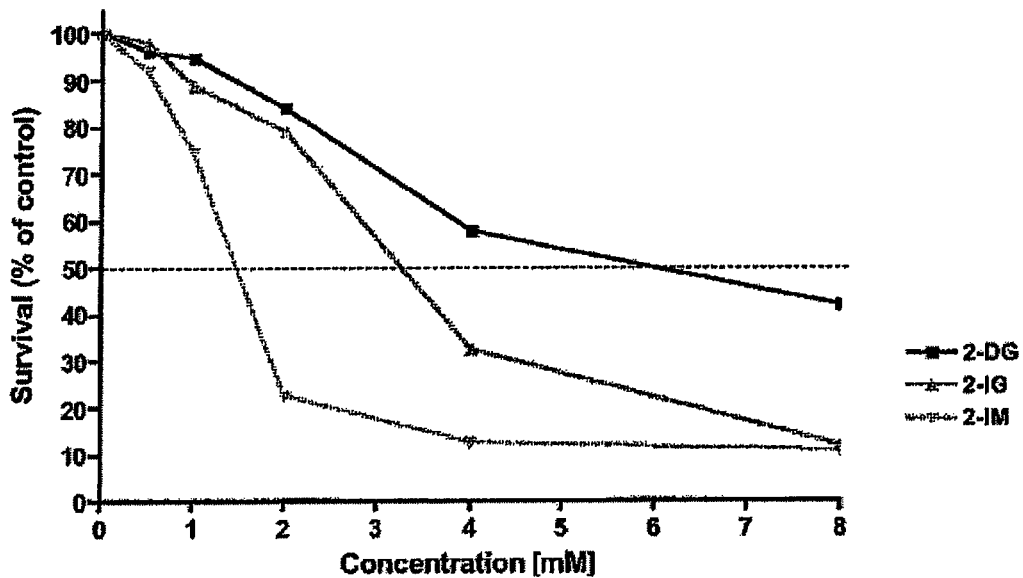
FIG. 5 shows activity comparison of 2-IM and 2-IG with 2-DG in glioma Colo357 pancreatic tumor.
Figure 9:
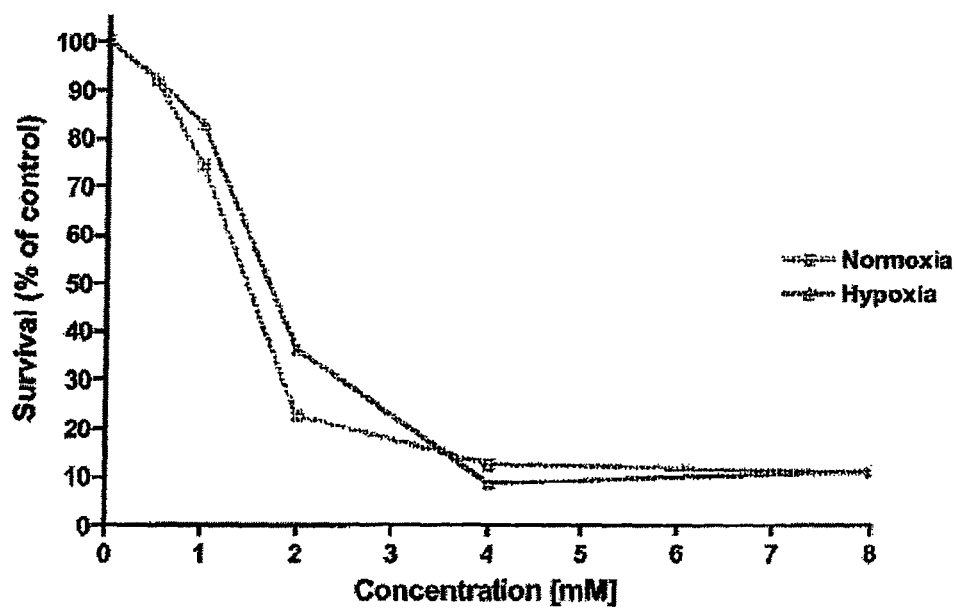
FIG. 9 shows activity comparison of 2-IM in Colo357-FG pancreatic tumor under normoxia and hypoxia.
Figure 10:
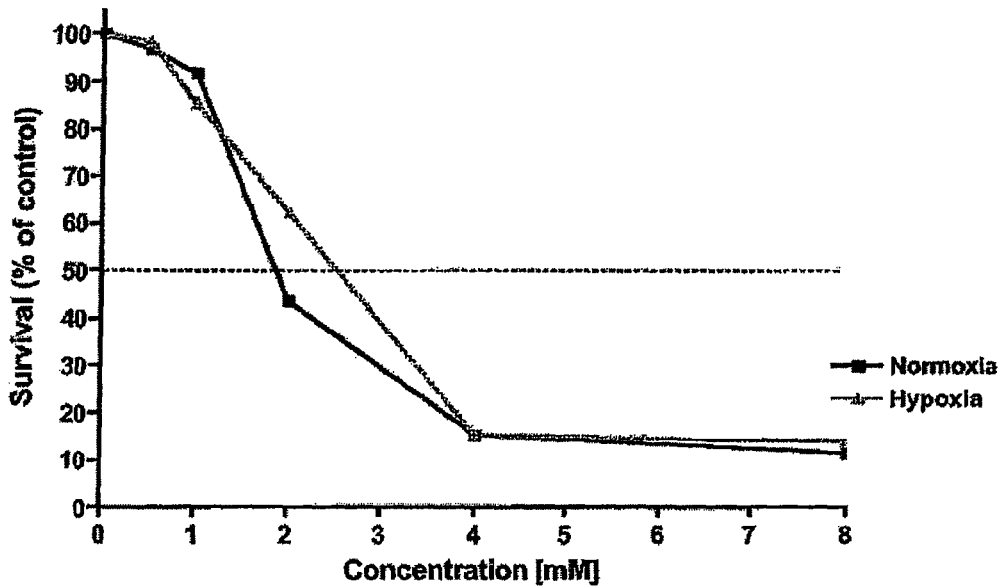
FIG. 10 shows activity comparison of 2-IM in Colo357-L3.6 pancreatic tumor under normoxia and hypoxia.
Figure 15:
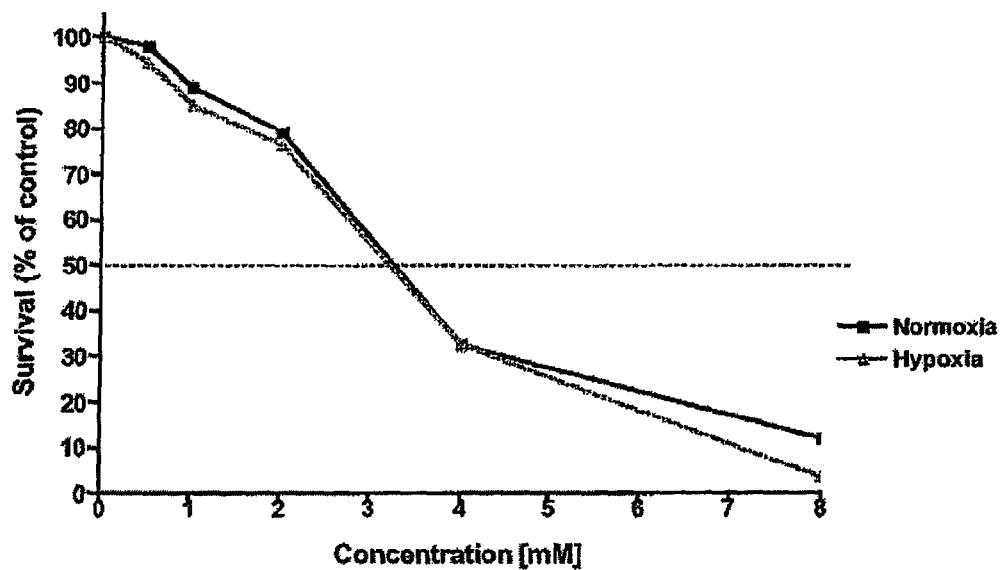
FIG. 15 shows activity comparison of 2-IG in Colo357-FG pancreatic tumor under normoxia and hypoxia.
Figure 16:
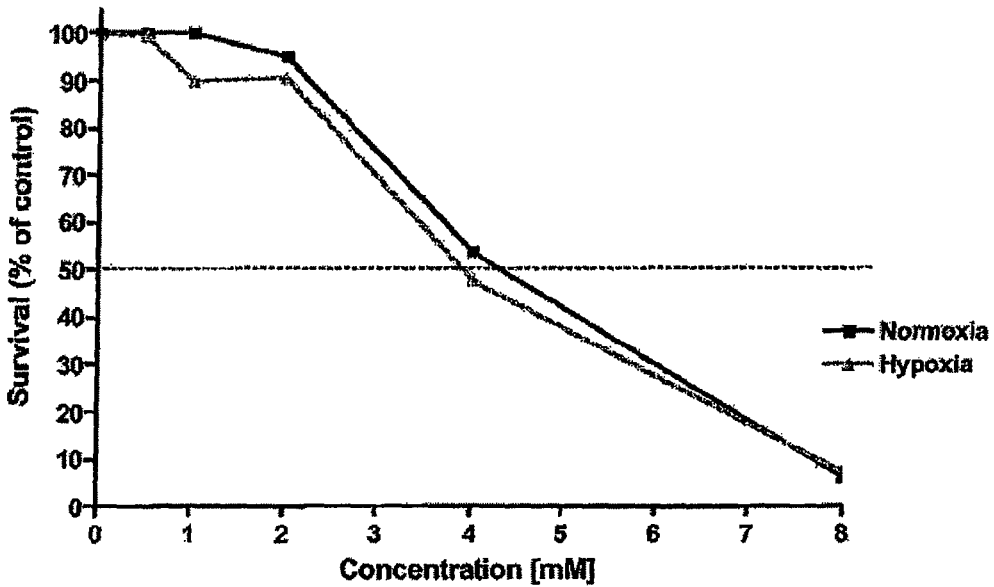
FIG. 16 shows activity comparison of 2-IG in Colo357-L3.6 pancreatic tumor under normoxia and hypoxia.

FIG. 5 shows activity comparison of 2-IM and 2-10 with 2-DG in glioma Colo357 pancreatic tumor. FIG. 9 shows activity comparison of 2-IM in Colo357-FG pancreatic tumor under normoxia and hypoxia. FIG. 10 shows activity comparison of 2-IM in Colo357-L3.6 pancreatic tumor under normoxia and hypoxia. FIG. 15 shows activity comparison of 2-IG in Colo357-FG pancreatic tumor under normoxia and hypoxia. FIG. 16 shows activity comparison of 2-IG in Colo357-L3.6 pancreatic tumor under normoxia and hypoxia.

Figure 11:
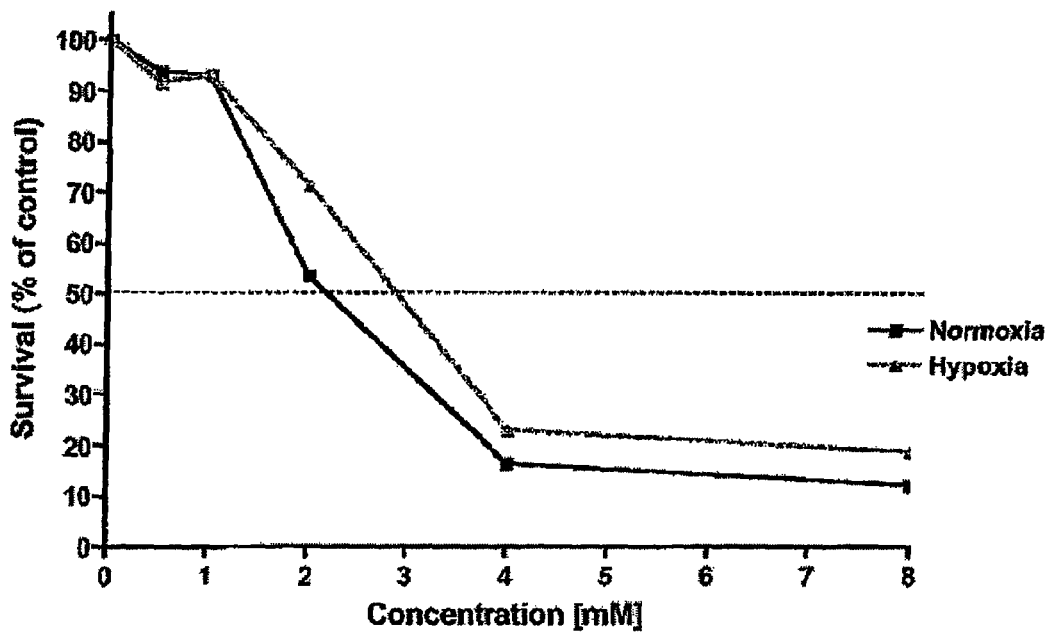
FIG. 11 shows activity comparison of 2-IM in AsPc-1 pancreatic tumor under normoxia and hypoxia.
Figure 17:
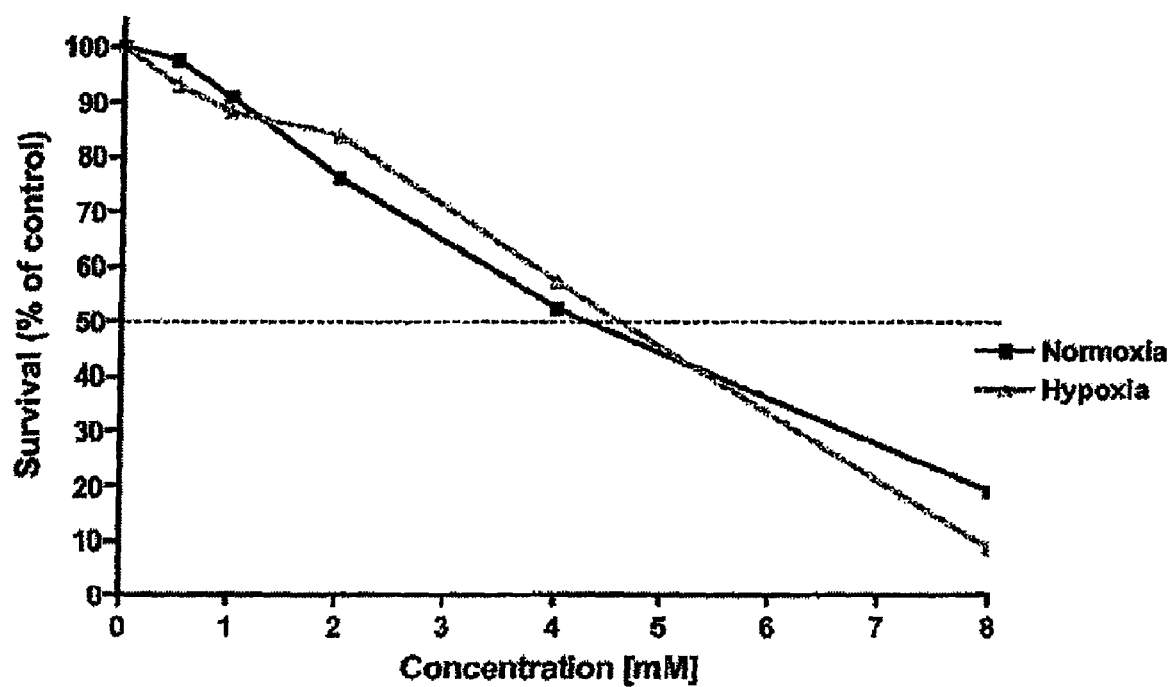
FIG. 17 shows activity comparison of 2-IG in AsPc-1 pancreatic tumor under normoxia and hypoxia.

FIG. 11 shows activity comparison of 2-IM in AsPc-1 pancreatic tumor under normoxia and hypoxia. FIG. 17 shows activity comparison of 2-IG in AsPc-1 pancreatic tumor under normoxia and hypoxia.

While specific embodiments of the disclosure have been shown and described in detail to illustrate the application of the principles of the disclosure, it will be understood that the disclosure may be embodied otherwise without departing from such principles.

We claim:

1. A pharmaceutical composition comprising an iodo-hexose compound having the structural formula:

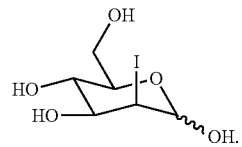

2. A composition comprising an iodo-hexose compound having the structural formula:

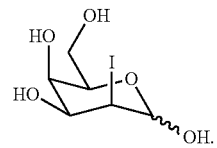

3. A method of treating glioblastoma or pancreatic cancer comprising the administration, to a patient in need thereof, of a therapeutically effective amount of at least one 2-deoxy-2-iodo-D hexose compound selected from the group consisting of 2-deoxy-2-iodo-D-mannose, 2-deoxy-2-iodo-D-talose, and 2-deoxy-2-iodo-D-galactose.

4. The method of claim 3 wherein the 2-deoxy-2-iodo-D-hexose compound is 2-deoxy-2-iodo-D-mannose.

5. The method of claim 3 wherein the 2-deoxy-2-iodo-D-hexose compound is 2-deoxy-2-iodo-D-talose.

6. The method of claim 3 wherein the 2-deoxy-2-iodo-D-hexose compound is 2-deoxy-2-iodo-D-galactose.

7. A method for achieving an effect in a patient comprising the administration of a therapeutically effective amount of at least one iodo-hexose compound selected from the group consisting of 2-deoxv-2-iodo-D-mannose, 2-deoxy-2-iodo-D-galactose, and 2-deoxy-2-iodo-D-talose, wherein the effect is reducing tumor growth resulting from at least one disease selected from the group consisting of pancreatic cancer and glioblastoma.

* * * * *